(12) United States Patent
Gregerson et al.

(10) Patent No.: US 9,526,461 B2
(45) Date of Patent: Dec. 27, 2016

(54) MULTI-PLANE X-RAY IMAGING SYSTEM AND METHOD

(71) Applicant: MOBIUS IMAGING, LLC, Ayer, MA (US)

(72) Inventors: Eugene A Gregerson, Bolton, MA (US); Russell Stanton, Lunenberg, MA (US); Michael Connor, Tyngsboro, MA (US); Michael Allen, Boxborough, MA (US); Paul Sebring, Townsend, MA (US); Robert Powell, Bolton, MA (US); Scott Coppen, Amesbury, MA (US)

(73) Assignee: MOBIUS IMAGING, LLC, Shirley, MA (US)

( * ) Notice: Subject to any disclaimer, the term of this patent is extended or adjusted under 35 U.S.C. 154(b) by 0 days.

(21) Appl. No.: 13/926,441

(22) Filed: Jun. 25, 2013

(65) Prior Publication Data

US 2013/0343509 A1 Dec. 26, 2013

Related U.S. Application Data

(60) Provisional application No. 61/664,437, filed on Jun. 26, 2012.

(51) Int. Cl.
*A61B 6/03* (2006.01)
*A61B 6/00* (2006.01)

(52) U.S. Cl.
CPC .............. *A61B 6/032* (2013.01); *A61B 6/035* (2013.01); *A61B 6/4014* (2013.01);
(Continued)

(58) Field of Classification Search
CPC .......... A61B 6/027; A61B 6/032; A61B 6/035; A61B 6/485; A61B 6/4014; A61B 6/4435; G01N 23/046; G01N 2223/419; G01T 1/1615
(Continued)

(56) References Cited

U.S. PATENT DOCUMENTS 5,499,415 A * 3/1996 McKenna .............. A61B 6/032
378/209
5,966,422 A 10/1999 Dafni et al.
(Continued)

FOREIGN PATENT DOCUMENTS

EP 2324768 A1 5/2011
JP 6453692 S 1/1989
(Continued)

OTHER PUBLICATIONS

Majdani et. al., Temporal Bone Imaging: Comparison of Flat Panel Volume CT and MulAug. 2009, Am. J. Neuroradiol. vol. 30, p. 1419, 1420.*
(Continued)

*Primary Examiner* — Glen Kao
(74) *Attorney, Agent, or Firm* — The Marbury Law Group, PLLC

(57) ABSTRACT

Imaging systems having multiple radiation sources, such as x-ray sources, and multiple radiation detectors, such as flat-panel x-ray detectors and/or diagnostic-quality CT detectors, housed within an imaging gantry, for obtaining simultaneous images of an object positioned within a bore of the gantry in multiple imaging planes.

21 Claims, 7 Drawing Sheets

(52) U.S. Cl.
CPC .......... *A61B 6/4028* (2013.01); *A61B 6/4085* (2013.01); *A61B 6/4266* (2013.01); *A61B 6/4405* (2013.01); *A61B 6/4435* (2013.01); *A61B 6/4476* (2013.01); *A61B 6/4482* (2013.01); *A61B 6/481* (2013.01); *A61B 6/485* (2013.01); *A61B 6/486* (2013.01); *A61B 6/504* (2013.01); *A61B 6/56* (2013.01)

(58) Field of Classification Search
USPC ........ 378/4, 5, 9, 11, 14, 15, 21, 41, 44, 62, 378/64, 92, 98, 98.8, 111, 126, 205, 901
See application file for complete search history.

(56) References Cited

U.S. PATENT DOCUMENTS

| | | | | |
|---|---|---|---|---|
| 6,097,788 | A * | 8/2000 | Berenstein et al. | 378/92 |
| 6,212,251 | B1 * | 4/2001 | Tomura et al. | 378/15 |
| 6,327,330 | B1 * | 12/2001 | Peter | A61B 6/032 378/15 |
| 6,823,039 | B2 * | 11/2004 | Hoheisel | A61B 6/032 378/19 |
| 7,108,421 | B2 * | 9/2006 | Gregerson | A61B 6/032 378/146 |
| 7,332,722 | B1 * | 2/2008 | Tran et al. | 250/363.09 |
| 2004/0062357 | A1 * | 4/2004 | Bair | 378/197 |
| 2004/0213371 | A1 | 10/2004 | Bruder et al. | |
| 2005/0013403 | A1 * | 1/2005 | Reznicek et al. | 378/15 |
| 2005/0135560 | A1 * | 6/2005 | Dafni et al. | 378/101 |
| 2006/0193430 | A1 * | 8/2006 | Kuhn | 378/9 |
| 2008/0013691 | A1 | 1/2008 | Gregerson et al. | |
| 2008/0101533 | A1 | 5/2008 | Ein-Gal | |
| 2008/0285707 | A1 | 11/2008 | Kalender et al. | |
| 2009/0252285 | A1 | 10/2009 | Shapiro et al. | |
| 2010/0025590 | A1 | 2/2010 | Luecke et al. | |
| 2010/0135454 | A1 * | 6/2010 | Noo | 378/9 |
| 2010/0220832 | A1 | 9/2010 | Ning et al. | |
| 2010/0246753 | A1 | 9/2010 | Mollov | |
| 2010/0290586 | A1 | 11/2010 | Friedrich | |
| 2011/0075796 | A1 * | 3/2011 | Loef et al. | 378/15 |
| 2011/0080992 | A1 * | 4/2011 | Dafni | 378/9 |
| 2011/0228910 | A1 | 9/2011 | Gregerson et al. | |
| 2011/0280380 | A1 | 11/2011 | Maschke | |
| 2012/0063564 | A1 | 3/2012 | Klingenbeck | |
| 2012/0099697 | A1 | 4/2012 | Helm et al. | |

FOREIGN PATENT DOCUMENTS

| | | |
|---|---|---|
| JP | 05007581 A * | 1/1993 |
| WO | 89/08269 A1 | 9/1989 |
| WO | 03/077763 A2 | 9/2003 |
| WO | 2005/004722 A2 | 1/2005 |

OTHER PUBLICATIONS

Kumamaru et. al., CT Angiography: Current Technology and Clinical Use, Mar. 2010, Radiol, Clin, North Am. vol. 48, No. 2, p. 213-219.*

Yin et. al., The Role of In-Room kV X-Ray Imaging for Patient Setup and Target Localization, Dec. 2009, American Association of Physicists in Medicine, Report of AAPM Task Group 104, p. 1, 8, 9.*

Dahi, Spatial resolution analysis of a variable resolution X-ray cone-beam computed tomography system, May 2009, PhD Thesis, The University of Memphis, p. 13, 15.*

International Search Report and Written Opinion issued in PCT Application No. PCT/US2013/047522 mailed on Oct. 18, 2013.

International Preliminary Report on Patentability (Chapter 1 of the Patent Cooperation Treaty) in International Application No. PCT/US2013/047522 dated Jan. 8, 2015.

Extended European Search Report from the Munich Patent Office in European Application No. 13810725.5-1666 / 2863803 based on International Search Report PCT/US2013/047522 dated Feb. 3, 2016.

Invitation to Proceed received from the European Patent Office in European Application No. 13810725.5-1666 / 2863803 based on International Search Report PCT/US2013/047522 dated Feb. 16, 2016.

* cited by examiner

MULTI-PLANE X-RAY IMAGING SYSTEM AND METHOD

RELATED APPLICATIONS

This application claims the benefit of priority to U.S. Provisional Application No. 61/664,437, filed Jun. 26, 2012, the entire contents of which are incorporated herein by reference.

BACKGROUND

There exist a number of x-ray diagnostic imaging systems, including 3D computed tomography (CT) scanners and 2D x-ray fluoroscopic imaging systems. Typically, they are located in a radiology department of a hospital or other medical facility. It would be beneficial to have a system that can provide a wide variety of diagnostic images at the point of care.

SUMMARY

Embodiments include an imaging system including an O-shaped imaging gantry having at least one radiation source and at least two radiation detectors for obtaining simultaneous images of an object positioned within a bore of the gantry in multiple imaging planes. In embodiments, the imaging system may include at least two x-ray radiation sources and at least two x-ray detectors positioned opposite the x-ray radiation sources for obtaining multi-planar images of the object in real-time.

In various embodiments, the gantry includes an outer shell defining a housing and a rotor that is positioned within and rotatable around the housing, wherein the radiation source(s) and detectors are secured to the rotor. Various additional components, such as a high-voltage generator, a rotor drive mechanism, a battery system and/or a computer, may be secured to the rotor.

In various embodiments, the system may provide 2D fluoroscopic images as well as 3D CT images.

In various embodiments, the system may be a mobile system.

Further embodiments include methods of imaging an object, such as a human or animal patient, that includes positioning an object with an imaging bore of an O-shaped imaging gantry having at least one radiation source and at least two radiation detectors, and obtaining simultaneous images of the object in multiple imaging planes.

BRIEF DESCRIPTION OF THE DRAWINGS

Other features and advantages of the present invention will be apparent from the following detailed description of the invention, taken in conjunction with the accompanying drawings of which.

DETAILED DESCRIPTION

This application is related to U.S. application Ser. No. 12/576,681, filed Oct. 9, 2009, now U.S. Pat. No. 8,118,488, U.S. application Ser. No. 13/025,566, filed Feb. 11, 2011, U.S. application Ser. No. 13/025,573, filed Feb. 11, 2011, U.S. application Ser. No. 13/441,555, filed Apr. 6, 2012, U.S. Provisional Application No. 61/658,650, filed Jun. 12, 2012, and U.S. Provisional Application No. 61/659,609, filed Jun. 14, 2012. The entire contents of all of these applications are hereby incorporated by reference for all purposes.

The various embodiments will be described in detail with reference to the accompanying drawings. Wherever possible, the same reference numbers will be used throughout the drawings to refer to the same or like parts. References made to particular examples and implementations are for illustrative purposes, and are not intended to limit the scope of the invention or the claims.

Various embodiments include imaging systems having multiple radiation sources, such as x-ray sources, and multiple radiation detectors, such as flat-panel x-ray detectors and/or diagnostic-quality CT detectors, housed within an imaging gantry, for obtaining simultaneous images of an object positioned within a bore of the gantry in multiple imaging planes.

Figure 1:
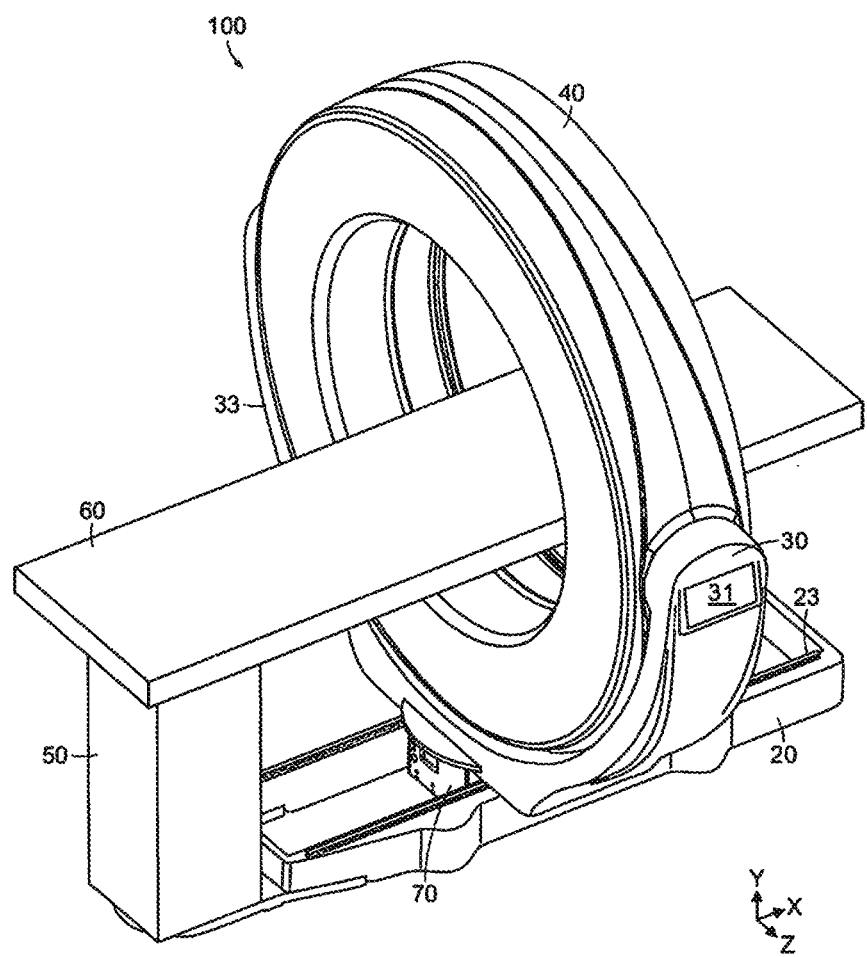
FIG. 1 is a perspective view of an imaging system in accordance with one embodiment of the invention.

An imaging system 100 according to one embodiment is shown in FIG. 1. The imaging system 100 may be a mobile imaging system 100, and may include a mobile base 20, a gimbal 30, a gantry 40, and a pedestal 50. The system 100 includes image collection components, such as multiple radiation sources and/or detectors that are housed within the gantry 40. The system 100 is configured to collect imaging data, such as, 2D x-ray fluoroscopic images and/or 3D x-ray tomographic image data, for example, from an object located within the bore 416 of the gantry 40, in any manner known in the medical imaging field. The pedestal 50 is configured to support a tabletop support 60 that may be attached to the pedestal 50 in a cantilevered manner and extend out into the bore of the gantry 40 to support a patient or other object being imaged.

The gimbal 30 may be a generally C-shaped support that is mounted to the top surface of base 20 and includes a pair of arms 31, 33 extending up from the base. The arms 31, 33 may be connected to opposite sides of gantry 40 so that the gantry is suspended above base 20 and gimbal 30. In one embodiment, the gimbal 30 and gantry 40 may rotate together about a first (e.g., vertical) axis with respect to the base 20, and the gantry 40 may tilt about a second (e.g., horizontal) axis with respect to the gimbal 30 and base 20. In embodiments, a drive mechanism may be mounted between the gimbal 30 and the base 20 to controllably drive the rotation (i.e., "yaw" motion) of the gimbal 30 and gantry 40 with respect to the base 20. A drive mechanism may also controllably drive the "tilt" motion of the gantry 40 with respect to the gimbal 30.

In certain embodiments, the gimbal 30 and gantry 40 may translate with respect to the base 20. The gimbal 30 may include bearing surfaces that travel on rails 23, as shown in FIG. 1, to provide the translation motion of the gimbal 30 and gantry 20. A scan drive mechanism may drive the translation of the gantry and gimbal relative to the base, and a main drive mechanism may drive the entire system in a transport mode (e.g., on one or more casters or wheels). In the embodiment of FIG. 1, both of these functions are combined in a drive system 70 that is located beneath the gimbal 30. Further details of a suitable drive system for a mobile imaging device are described in U.S. application Ser. No. 13/025,566, filed Feb. 11, 2011, which has been incorporated herein by reference.

In certain embodiments, the base 20 of the system may be omitted, and the gimbal 30 may sit directly on the ground to support the gantry 40. In other embodiments, the gimbal may be omitted, and the gantry 40 is a stand-alone gantry that may sit on the ground, or is otherwise supported.

Figure 2:
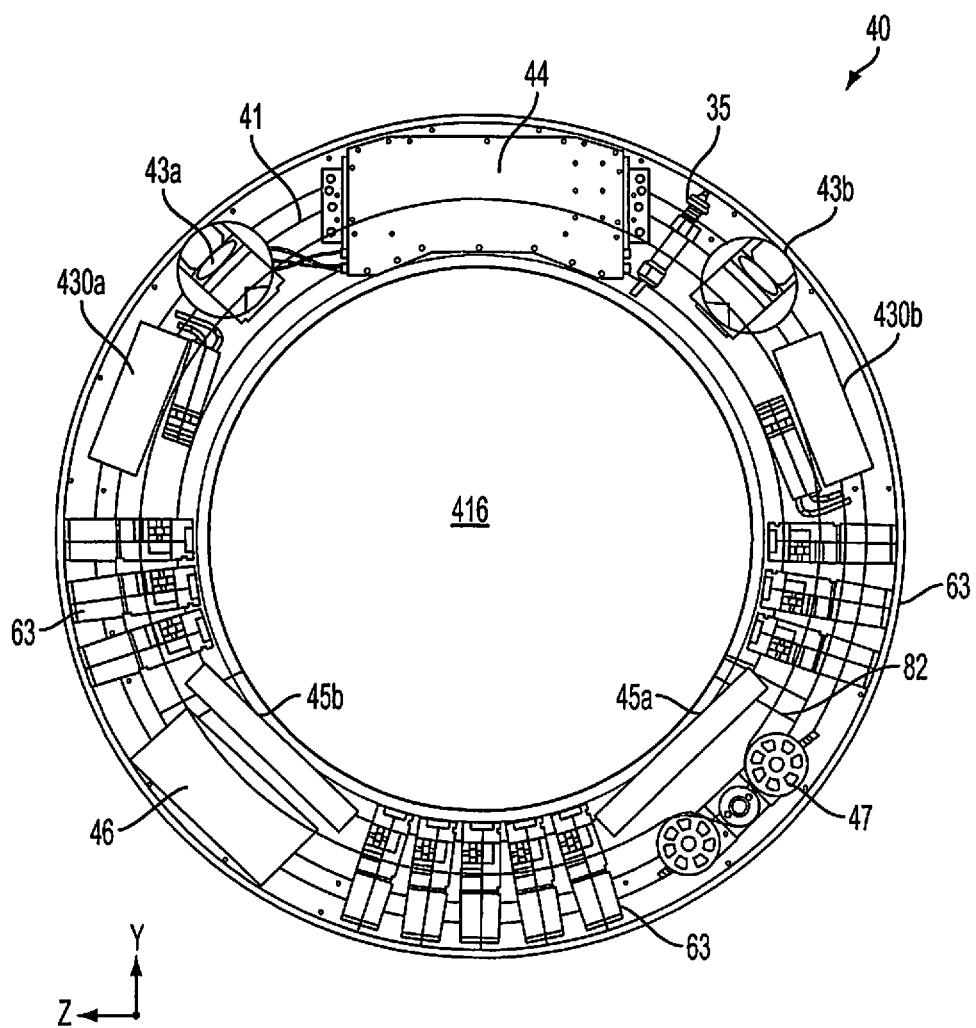
FIG. 2 is a cross-sectional view of an imaging gantry having multiple radiation sources and multiple radiation detectors for obtaining simultaneous images of an object positioned within a bore of the gantry in multiple imaging planes.

FIG. 2 is a cross-sectional view of the gantry 40 showing a number of components of the imaging system according to one embodiment. The gantry 40 may be an O-shaped gantry ring defining an imaging bore 416. A first radiation source 43*a* may be located on an opposite side of the gantry 40 from a first radiation detector 45*a* to obtain images of an object positioned within the bore 416 in a first imaging plane. A second radiation source 43*b* may be located on an opposite side of the gantry 40 from a second radiation detector 45*b* to obtain images of the object in a second imaging plane, different from the first imaging plane. The first imaging plane and the second imaging plane may be offset from one another by a known angle, such as 90°, or any suitable angle (e.g., greater than 0° and less than 180°). The offset may be fixed, or in some embodiments, may be variable such that the position of one radiation source/detector pair may be movable on the gantry ring with respect to the other source/detector pair. Radiation imaging beams from both sources 43*a*, 43*b* may be directed through a common isocenter within the bore 416. The multiple radiation sources 43*a*, 43*b* and detectors 45*a*, 45*b* may be mounted to a rotor 41 that may be rotated around the interior of the gantry 40 to any desired imaging angle. For example, the rotor 41 may be rotated within the gantry 40 to a position such that a first source 43*a* and detector 45*a* pair may obtain anterior-posterior (AP) images of a region of interest of a patient located within the bore 416, while a second source 43*b* and detector 45*b* pair may simultaneously obtain lateral images of the same region of interest. In some embodiments, the rotor 43 may be rotated around the interior of the gantry (e.g., 360°) while one or both source/detector pairs are obtaining image data to obtain a 3D tomographic image (e.g., a cone-beam CT reconstruction). Various embodiments may be used, for example, for performing anatomic (e.g., arterial, cardiac, spinal, etc.) imaging of a human or animal patient.

In embodiments, a power supply for the radiation source(s) 43*a*, 43*b* may be provided within the gantry, such as on the rotor 41. The power supply may be a high-voltage generator 44. In embodiments, a high-voltage generator may provide high-voltage power to multiple radiation sources (e.g., x-ray tubes). The system 100 may include control circuitry that enables provision of high-voltage power from the high-voltage generator 44 to alternate between multiple radiation sources 43*a*, 43*b*. For example, power from the high-voltage generator 44 may be provided to a first source 43*a* for a first time period, and then to a second source 43*b* for a second period, and the process may then be repeated. The high-voltage generator 44 may thus provide "pulsed" high voltage power to multiple radiation sources (e.g., x-ray tubes) sequentially, preferably at a high-rate.

The pulse duration of each high-voltage power pulse delivered to the radiation sources may be between 0.1-100 milliseconds, such as 1-50 milliseconds (e.g., 5-30 milliseconds, such as ~15 milliseconds). For example, a 15 millisecond high voltage power pulse may be provided to the first source 43*a*, and then a 15 millisecond high voltage power pulse may be provided to the second source 43*b*. The first source 43*a* may not be exposing (i.e., generating a radiation beam) while the second source 43*b* is, and vice versa. Interaction between the two beams, which may result in blurring of the images, may be avoided. If there are more than two sources or other components requiring high voltage power, the high voltage generator 44 may provide high voltage power pulse(s) to these component(s). The high voltage generator 45 may then provide another pulse to the first source 43*a*, and the process may repeat.

In embodiments, during the first time period, while the first source 43*a* generates a radiation beam, the first detector 45*a* may be exposed to radiation that has been attenuated by an object within the imaging bore 416 and may collect imaging data for the object. The second source 43*a* may not be generating radiation 43*a*, and the second detector 45*b* may not be exposed to radiation or collecting imaging data. The second detector 45*b* may read out imaging data collected during a previous exposure. During the second time period, when the first source 43*a* is not generating radiation and the second source 43*b* is generating radiation, the first detector 45*a* is not being exposed to radiation and may read out the imaging data collected during the first time period. The second detector 45*b* may be exposed to radiation and may collect imaging data. The entire cycle (e.g., first time period and second time period) may repeat at more or less than 30 cycles (e.g., frames) per second. As used herein, obtaining "simultaneous" images includes embodiments in which multiple detectors are exposed to attenuated radiation and collect image data at the same time, as well as embodiments in which the detectors are rapidly multiplexed, such that when at least one first detector is collecting imaging data at least one second detector is reading out its just-collected imaging data, followed immediately by the at least one first detector reading out its just-collected imaging data while the at least one second detector collects additional imaging data, and so on.

While the embodiment illustrated in FIG. 2 illustrates a single high voltage generator 45 powering two sources 43*a*, 43*b*, it will be understood that in various embodiments multiple high voltage generators 45 may be provided on the gantry, and each radiation source 43*a*, 45*b* may have a dedicated high voltage generator. In some embodiments, one or more high voltage generators may be provided off the gantry 40 and high voltage power may be delivered to the radiation sources 43*a*, 43*b* via a cable or slip ring system.

Also, while the embodiment illustrated in FIG. 2 illustrates two source/detector pairs on the gantry 40, it will be understood that in various embodiments more than two source/detector pairs may be provided on the gantry.

The radiation sources 43*a*, 43*b*, which may be x-ray tubes, may each have a cooling system 430*a*, 430*b* for removing heat from the sources 43*a*, 43*b*, as is shown in FIG. 2.

The high voltage generator 43 may be powered by a power source on the gantry, such as a battery system 63. As shown in FIG. 2, the battery system 63 may be mounted to and rotates with the rotor 41. The battery system 63 may include a plurality of electrochemical cells. The cells may be incorporated into one or more battery packs. The battery system 63 is preferably rechargeable, and may be recharged by a charging system between imaging operations, such as when the rotor 41 is not rotating. In one embodiment, the battery system 63 consists of lithium iron phosphate (LiFePO$_4$) cells, though it will be understood that other suitable types of batteries can be utilized.

The battery system 63 provides power to various components of the imaging system 100. In particular, since the battery system 63 is located on the rotor 41, the battery system 63 may provide power to any component on the rotor 41, even as these components are rotating with respect to the non-rotating portion of the imaging system 100. Specifically, the battery system 63 is configured to provide the voltages and peak power required by the generator 45 and radiation sources 43a, 43b (e.g., x-ray tubes) to perform an imaging scan. For example, a battery system may output ~360V or more, which may be stepped up to 120 kV at the high-voltage generator 45 to perform an imaging scan. In addition, the battery system 63 may provide power to operate other components, such as an on-board computer 46, the detector arrays 45a, 45b, and the drive mechanism 47 for rotating the rotor 41 within the gantry 40.

It will be understood that in embodiments, power to the rotating portion of the system may be delivered from the non-rotating portion via a cable or slip ring system, for example.

In embodiments, the system 100 includes a rotor drive mechanism 47 that may drive the rotation of the rotor 41 around the interior of the gantry 40. The rotor drive mechanism 47 may be controlled by a system controller that controls the rotation and precise angular position of the rotor 41 with respect to the gantry 40, preferably using position feedback data, such as from a position encoder device. The rotor drive mechanism 47 may include a motor and gear system mounted to the rotor 41, as shown in FIG. 2. The motor may drive a gear that may be engage with a mating component on the non-rotating portion of the system to drive the rotation of the rotor. For example, a belt 82 may be rotatably fixed on the non-rotating portion of the system (e.g., the outer shell of the gantry 40), such as on a circumferential rail. The drive system 47 may engage with the belt 82 to drive the rotation of the rotor 41 within the gantry 40. The drive system 47 may be powered by battery system 63. The drive system 47 may be secured to the rotor 41 and may be positioned behind a detector 45a, as shown in FIG. 2. Further details of a suitable rotor drive system 47 are described in U.S. application Ser. No. 13/441,555, filed Apr. 6, 2012, which has been incorporated herein by reference.

A computer 46 may be provided on the rotating portion of the system, and may be secured to rotor 41 in a suitable location, such as behind a detector 45b, as shown in FIG. 2. The computer 46 may be powered by battery system 63. The computer 46 may be any suitable computing device, and may include one or more processors having associated memory that may execute instructions (e.g., software) stored in memory, as is known in the art. The computer 63 may perform various control functions for the various components on the rotor 41, and may serve as an interface between components on the rotor 41 and other components of the system 100. The computer 63 may be configured to receive imaging data collected by the detectors 45a, 45b. For example, the detectors 45a, 45b may stream their image data over a suitable data connection (e.g., wired or wireless) to the computer 46. The computer 46 may store, process and/or transmit the imaging data. For example, the computer 46 may include or may be coupled to a wireless transmitter that may transmit the data to another logical entity, such as to an external workstation and/or to another computer located on the non-rotating portion of the system (e.g., in gimbal 30). This may enable real-time display of the collected imaging data.

A docking system 35 may be provided for connecting the rotating portion of the system 100 to the non-rotating portion between imaging scans. The docking system 35 may include a connector for carrying power between the rotating and non-rotating portions. In embodiments, the docking system 35 may be used to provide power to the battery system 63 such that the batteries may be charged using power from an external power source (e.g., grid power). The docking system 35 may also include a data connection to allow data signals to pass between the rotating and non-rotating portions. Further details of a suitable docking system are described in U.S. application Ser. No. 13/441,555, filed Apr. 6, 2012, which has been incorporated herein by reference.

Figure 3:
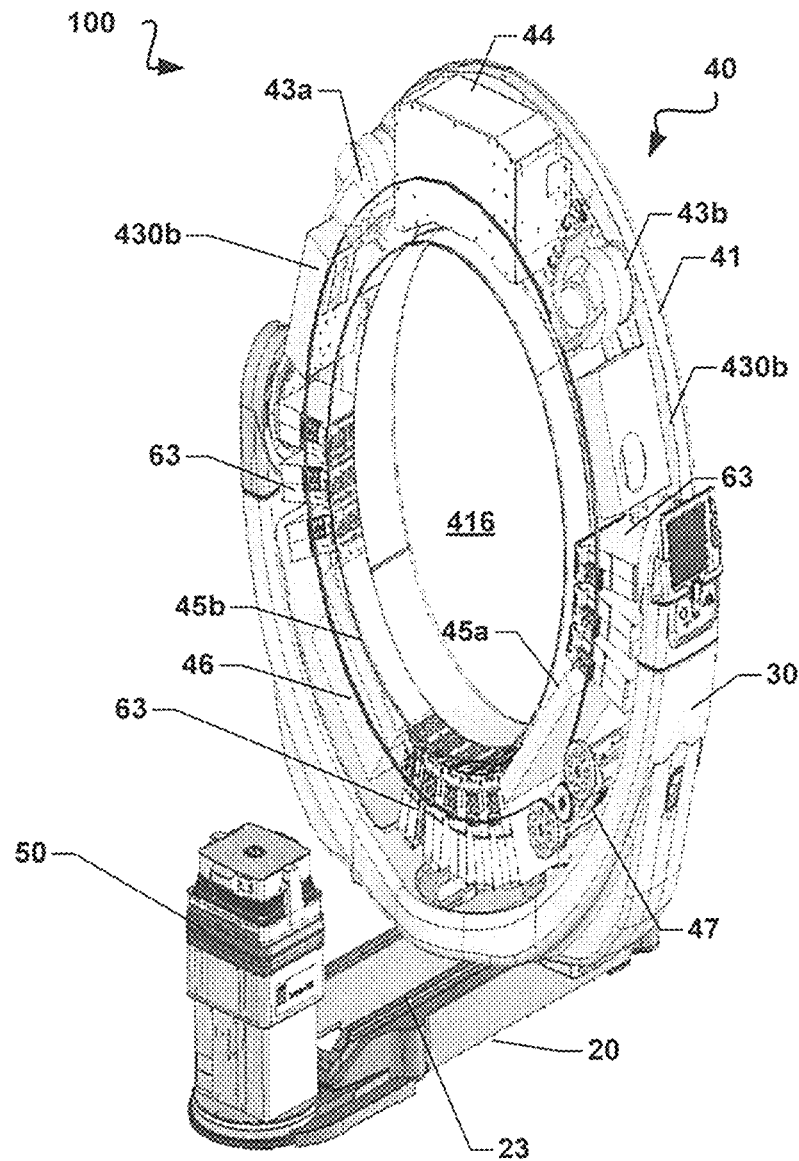
FIG. 3 is a perspective view of the imaging system of FIGS. 1 and 2 with the outer shell of the gantry removed.
Figure 4:
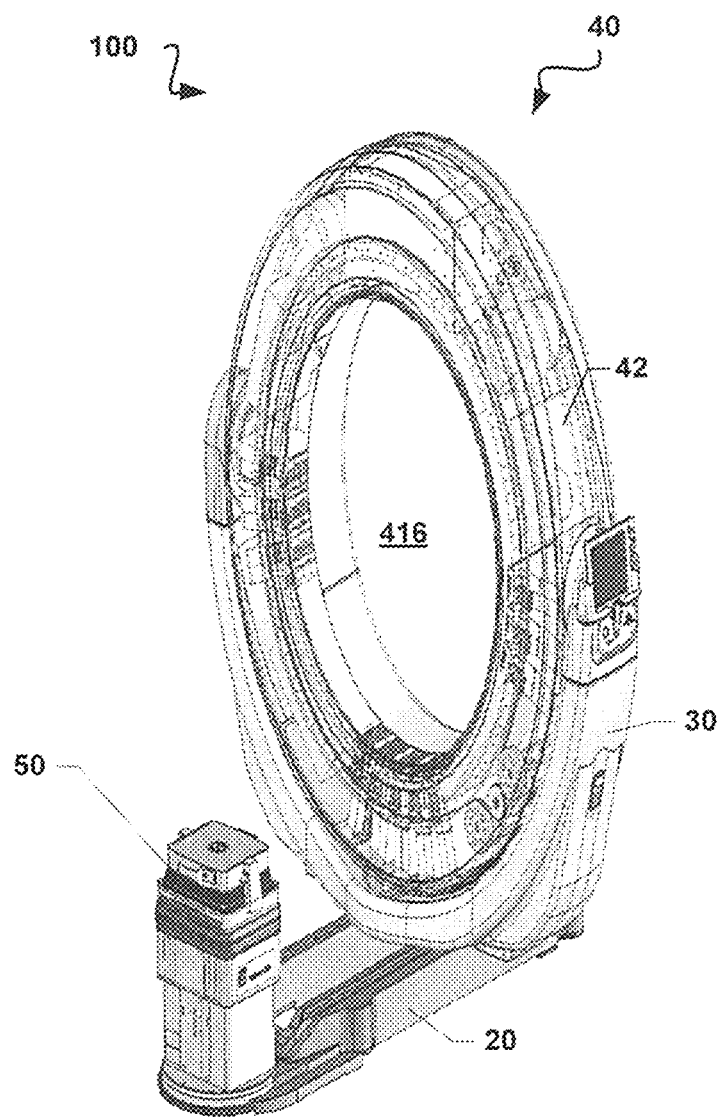
FIG. 4 is a perspective view of the imaging system of FIGS. 1 and 2 with the outer shell of the gantry rendered transparent.

FIGS. 3 and 4 are perspective views of a system 100 according to one embodiment. In FIG. 3, the outer shell of the gantry 40 is not shown to more clearly illustrate the various components secured to rotor 41. FIG. 4 shows the system 100 with the outer shell 42 of the gantry 40 rendered transparent. In various embodiments, the system 100 may provide mobile bi-plane imaging, such as x-ray fluoroscopic imaging. The rotor 41 may rotate to any angle to obtain images in any desired imaging plane. The radiation sources 43a, 43b and detectors 45a, 45b may be mounted to a rigid, circular rotor 41, which may inhibit relative movement of the imaging components during a scan, such as flexing towards or away from the bore 416. Further, the entire rotor 41 assembly may be housed within a rigid outer shell of the gantry 42, as shown in FIG. 4, which may further constrain the rotor 41 and prevent relative movement of the imaging components.

The system 100 may be used to perform arterial "road mapping" imaging, according to one embodiment. It is often the case that a physician would like to get a picture of the arterial anatomy over all or a portion of a patient's body. What is typically done is a contrast agent is injected at a first location in the patient, and an imaging device (such as an x-ray fluoroscopic C-arm device) is manually moved to various locations along the patient's body to capture images as the contrast agent works its way through the body and into the patient's extremities. The various images may be combined to provide a fuller image (or roadmap) of the patient's arterial anatomy. A system 100 of the present invention may be used to provide an arterial roadmap (e.g., a single plane roadmap, or a bi-plane roadmap). A contrast agent may be injected into a patient positioned within the bore 416 of the system. The gantry 40 and gimbal 30 may be driven along rails 23 on the base 20 to obtain arterial images as the contrast agent works its way through the patient. The movement of the gantry 40 and gimbal 30 on the rails may be controlled by an operator, or may be controlled automatically by a pre-programmed road mapping tracking controller, which may track the flow of contrast agent within the region of interest of the patient based on a known or likely flow path of the contrast agent over time. In embodiments, an image analysis of the flow of contrast agent in one or more arteries of the patient may be used to determine automatically the velocity of the gantry 40 (e.g, how quickly the gantry should translate down the patient axis), as the gantry 40 translates on the base 20.

The system 100 may further be used to perform cone beam CT imaging. The rotor 41 may rotate within the gantry 40 while one or both detectors 45a, 45b obtain images. The image data may then be reconstructed using a tomographic algorithm as is known in the art to obtain a 3D reconstructed image of the object. In embodiments, both detectors 45a, 45b may obtain images which may be combined for the reconstruction. Thus, in some embodiments, the rotor 41 may only need to rotate a portion of the distance that would normally be required (e.g., a 90° rotation of the rotor 41 may enable the detectors to scan 180° of the object, a 270° rotation of the rotor 41 enables a full 360° scan of the object). In embodiments, images captured from different detectors 45a, 45b may be interleaved when performing the cone-beam reconstruction. This may enable faster and/or more detailed scans.

In various embodiments, the gantry 40 and gimbal 30 may be translated along rails 23 during cone beam CT imaging to provide a helical cone beam CT scan. In various embodiments, a helical cone beam scan may be coordinated with the injection of a contrast agent to provide a three-dimensional arterial roadmap image.

Figure 5:
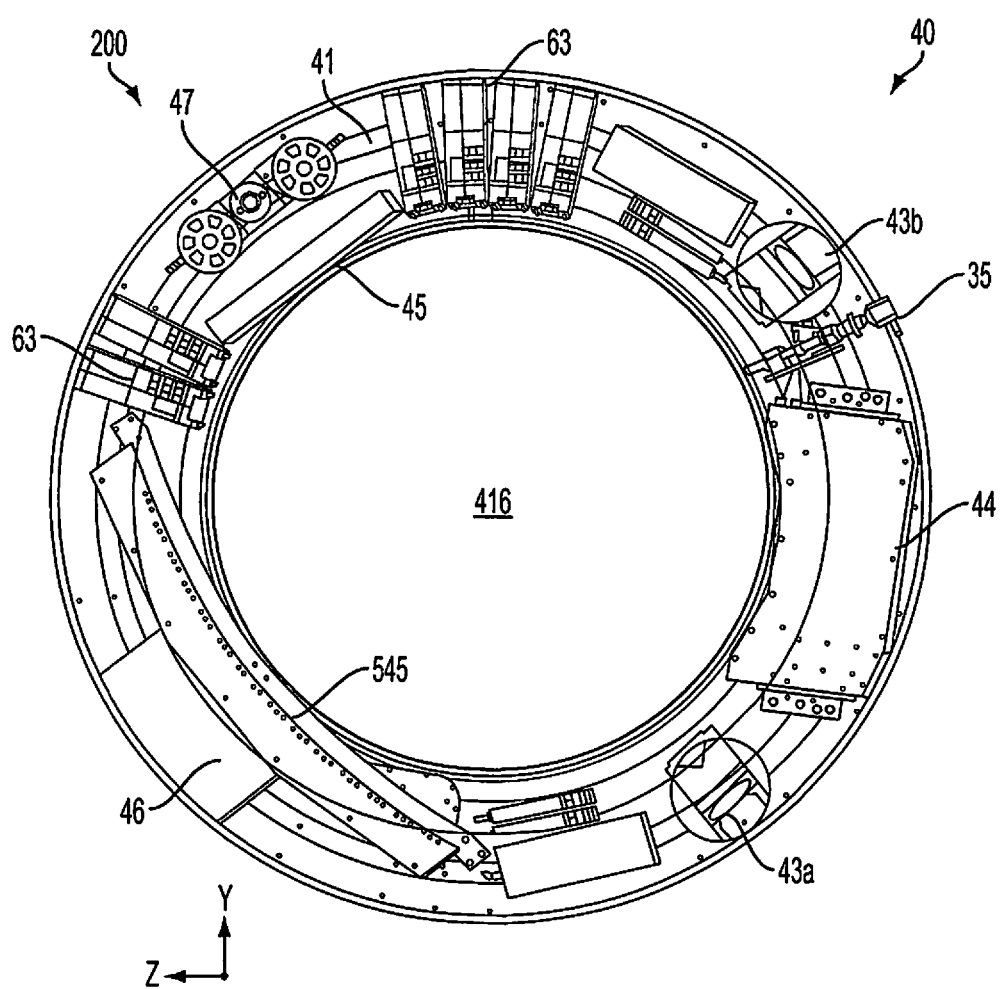
FIG. 5 is a cross-sectional view of an imaging gantry having multiple different types of radiation detectors.
Figure 6:
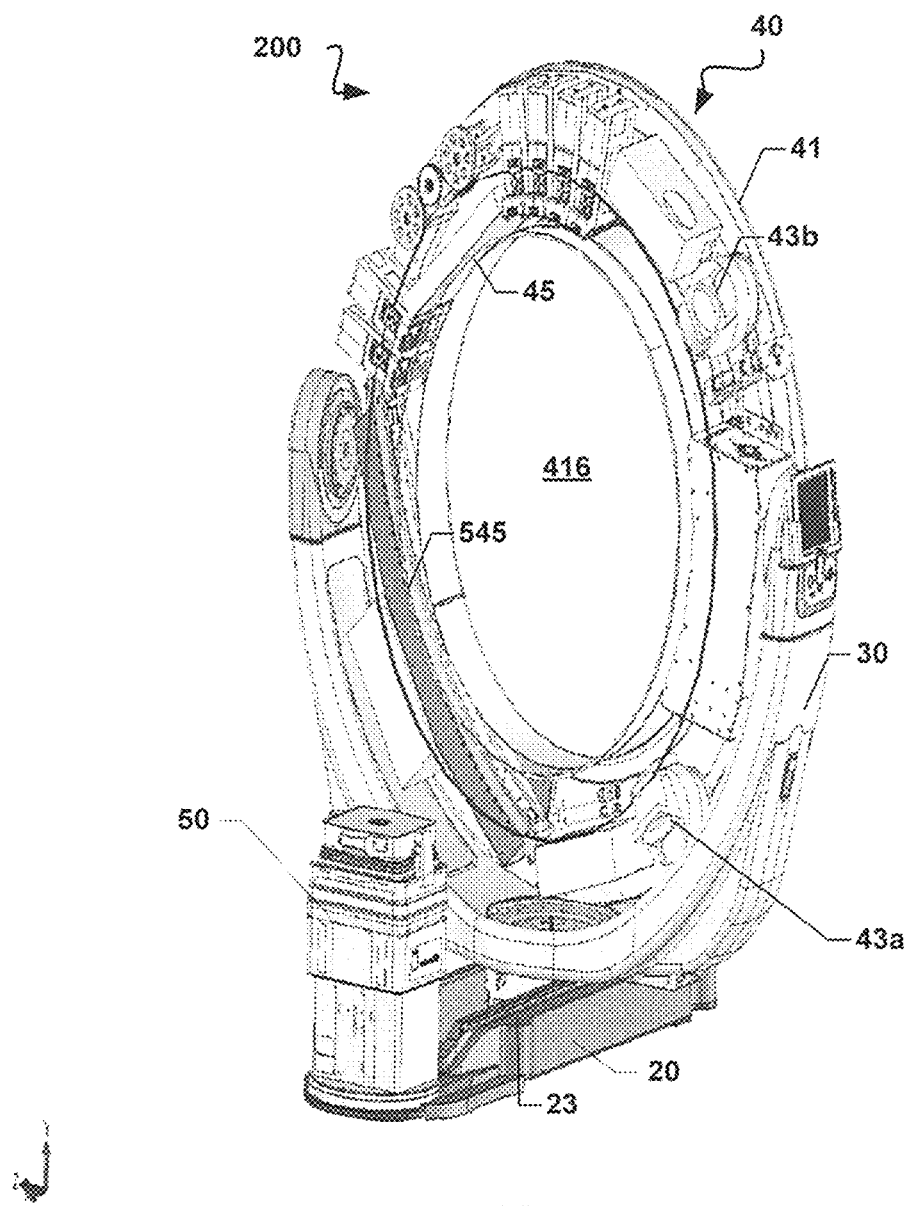
FIG. 6 is a perspective view of the imaging system of FIG. 5

FIGS. 5 and 6 illustrate an embodiment system 200 having multiple different types of detectors. Each different type of detector may be used to collect different types of images. As shown in FIG. 5, for example, a first radiation source 43a, such as an x-ray tube, may direct radiation to a first detector 45, which may be a flat panel detector of the type used for x-ray fluoroscopy as described above. A second radiation source 43b, which may also be an x-ray tube, may direct radiation to a second detector 545, which may be a diagnostic-quality CT detector. True CT detectors may be up to a meter or more in length, and may be comprised of a plurality of detector elements (e.g., cadmium tungstate material coupled to a photodiode) that may be arranged to form or approximate a semicircular arc centered on the focal spot of the radiation source 43b opposite the detector 545. Such detectors may provide relatively high-resolution images, which may include soft tissue images, over a wide field-of-view (e.g., may image a cross-sectional area within the bore having a diameter of 50 cm or more, as opposed to ~20 cm with a typical flat panel detector). These detectors 545 are typically narrower in the axial direction (i.e., along the length of the patient/object), and may have a width of less than 10 cm (e.g., 64 mm). Thus, these detectors 545 may image a relatively narrow "slice" of the object at a time. In contrast, flat panel detectors may be significantly wider in the axial direction (e.g., 30-40 cm), and thus may capture a much larger axial "slice" of the object at a given time. However, in various embodiments, the axial field of view a CT detector 545 and/or a flat panel detector 45 may be extended by translating the gantry 40 with respect to the patient, such as on rails 23.

In various embodiments, real time x-ray fluoroscopic images and diagnostic quality 3D CT image reconstructions may be provided using a single device 200. A flat panel detector 45 may provide real time x-ray fluoroscopic images in a first imaging plane. A CT detector 545 may optionally provide additional real time fluoroscopic images in a second imaging plane. The CT detector 545 may also be rotated about the patient to provide true x-ray CT 3D image reconstructions, including helical CT scan images. Alternatively or in addition, the flat panel detector 45 may be used to provide cone beam CT 3D image reconstructions.

A high-voltage generator 44 may provide high-voltage power to the radiation sources 43a, 43b, as described above. In embodiments, the high-voltage generator 44 may generate a pulsed power signal to one or more radiation sources for fluoroscopy applications, and may generate continuous power to one or more radiation sources for CT scanning.

Various embodiments may include a single radiation source 43, such as an x-ray tube, that is configured to direct radiation, including collimated x-ray radiation, onto multiple detectors, such as detectors 43a, 43b shown in FIGS. 2-4 and detectors 45, 545 shown in FIGS. 5-6. The radiation source 43 may include a beam steering mechanism that may alter the direction of the output beam by a particular angle, such as 90° or more, such that at least a portion of the output radiation beam is alternately centered on a first detector 45a and a second detector 45b, which may be spaced by 90° to provide bi-planar imaging, as described above.

Various embodiments of the imaging system 100 may be relatively compact. Various components may be designed to fit efficiently within the housing of the gantry 40. For example, high voltage generator 44 may have one or more angled or curved surfaces to accommodate the curvature of the rotor 41 and/or gantry 40. The battery system 63 may also include angled or curved surfaces to accommodate the curvature of the rotor 41 and/or gantry 40.

A further way in which the system 100 may be made compact is in the design of the gantry 40 and its interface with the rotating portion 101 (e.g., the rotor 41 and the various components mounted to the rotor 41). In embodiments, the outer shell 42 of the gantry 40 may comprise both a protective outer covering for the rotating portion and a mounting surface for a bearing that enables the rotating portion 101 to rotate 360° within the outer shell 42 of the gantry 40.

Figure 7A:
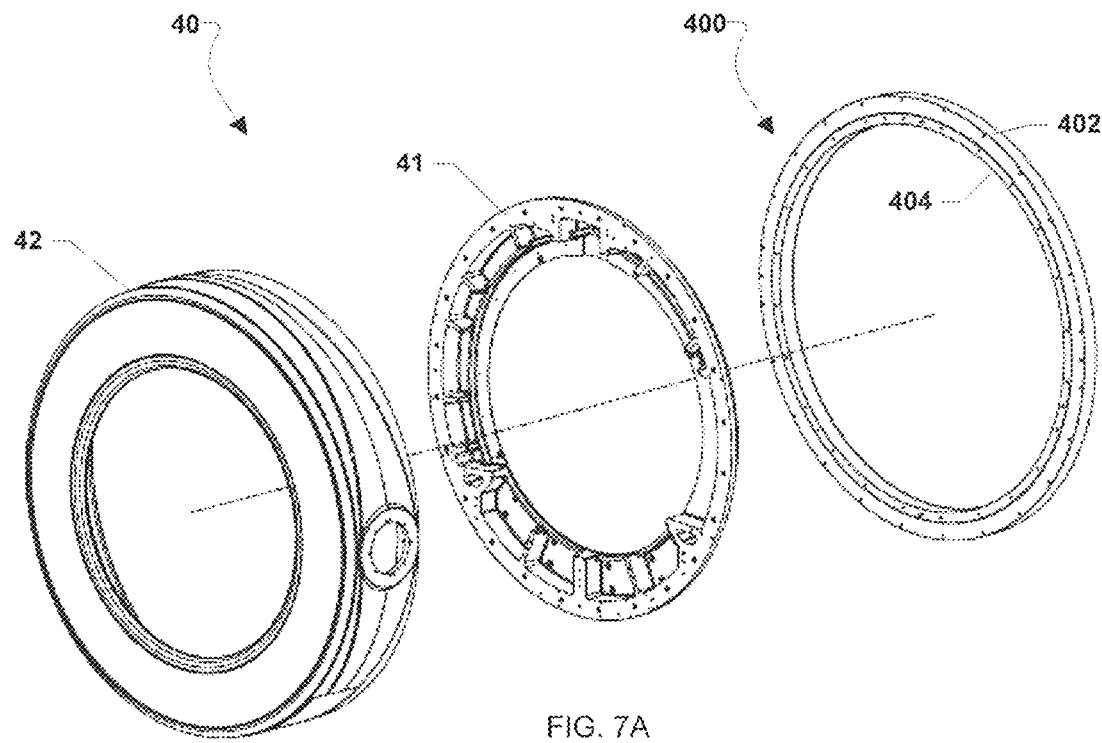
FIG. 7A is an exploded view of a gantry illustrating an outer shell, a rotor and a bearing system according to one embodiment.
Figure 7B:
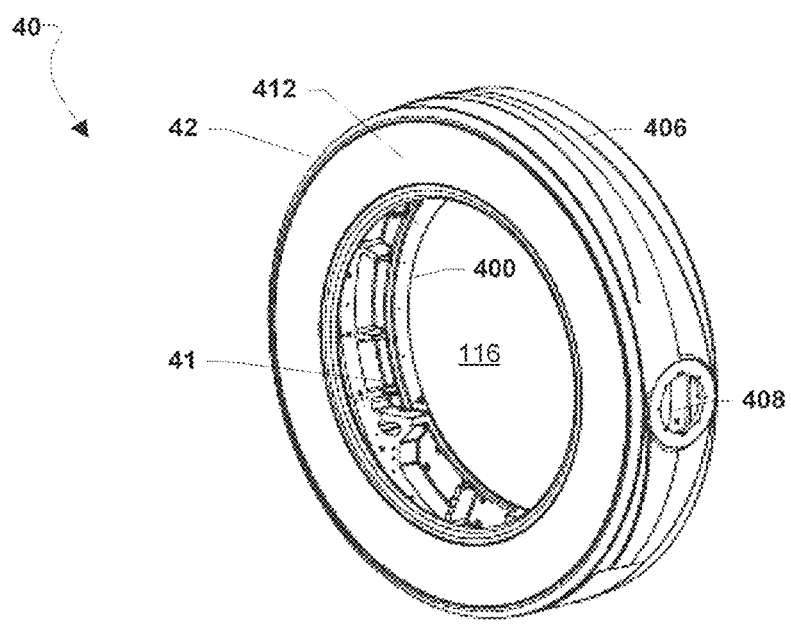
FIG. 7B is a perspective view of the assembled gantry.

FIG. 7A is an exploded view of a gantry 40 according to one embodiment that illustrates the outer shell 42, the rotor 41 and a bearing assembly 400. FIG. 7B illustrates the assembled gantry 40. As is shown in FIGS. 6A-B, the outer shell 42 of the gantry 40 may be a generally O-shaped covering of a structural material that may at least substantially fully enclose the rotating portion 101, including the rotor 41 and any components mounted to the rotor, over one or more sides of the rotating portion 101. The outer shell 42 of the gantry 40 may be conceptually considered an "exoskeleton," that both supports the rotating portion 101 of the system 100, preferably in three dimensions, and also provides a protective barrier between the rotating portion 101 and the external environment. The outer shell 42 may be fabricated from a sufficiently rigid and strong structural material, which may include, for example, metal, composite material, high-strength plastic, carbon fiber and combinations of such materials. In preferred embodiments, the outer shell 42 may be comprised of a metal, such as aluminum. The outer shell 42 may be machined or otherwise fabricated to relatively tight tolerances. The outer shell 42 may be formed as a one piece, unitary component. In other embodiments, the outer shell 42 may be comprised of multiple components and/or materials that may be joined using any suitable technique to provide the shell 42.

The outer shell 42 may have an outer circumferential surface 406 that may extend around the periphery of the rotating portion 101 of the system 100 to substantially fully enclose the rotating portion 101 around its outer circumference. The outer shell 42 may also include at least one side wall 412 that may extend from the outer circumferential surface 406 to a bore 416 of the gantry 40 and may substantially fully enclose the rotating portion 101 around one side of the rotating portion.

The bearing assembly 400 according to one embodiment is shown in FIG. 7A. In this embodiment, the bearing assembly 400 includes a first race 402 that may be securely fastened to the outer shell 42 of the gantry 40, and a second race 404 that may be securely fastened to the rotor 41. A bearing element is provided between the first race 402 and the second race 404, and is configured to allow the second race 404 (along with the rotor 41 to which it is attached) to rotate concentrically within the first race 402, preferably with minimal friction, thereby enabling the rotor 41 to rotate with respect to the outer shell 42 of the gantry 40. In some embodiments, all or a portion of the bearing assembly 400 may be integrally formed as a part of the outer shell 42 or of the rotor 41, or of both. For example, the first race 402 may be formed as an integral surface of the outer shell 42 and/or the second race 404 may be formed as an integral surface of the rotor 41. In various embodiments, the entire bearing assembly for enabling the rotation of the rotating portion 101 with respect to the non-rotating portion 103 of the imaging system 100 may be located within the generally O-shaped gantry 40.

The outer diameter of the gantry 40 can be relatively small, which may facilitate the portability of the system 100. In a preferred embodiment, the outer diameter of the gantry 40 is less than about 70 inches, such as between about 60 and 68 inches, and in one embodiment is about 66 inches. The outer circumferential wall 406 of the outer shell 42 may be relatively thin to minimize the OD dimension of the gantry 40. In addition, the interior diameter of the gantry 40, or equivalently the bore 116 diameter, can be sufficiently large to allow for the widest variety of imaging applications, including enabling different patient support tables to fit inside the bore, and to maximize access to a subject located inside the bore. In one embodiment, the bore diameter of the gantry 40 is greater than about 38 inches, such as between about 38 and 44 inches, and in some embodiments can be between about 40 and 50 inches. In one exemplary embodiment, the bore has a diameter of about 42 inches. The gantry 40 generally has a narrow profile, which may facilitate portability of the system 100. In one embodiment, the width of the gantry 40 (W) is less than about 17 inches, and can be about 15 inches or less.

The foregoing method descriptions are provided merely as illustrative examples and are not intended to require or imply that the steps of the various embodiments must be performed in the order presented. As will be appreciated by one of skill in the art the order of steps in the foregoing embodiments may be performed in any order. Words such as "thereafter," "then," "next," etc. are not necessarily intended to limit the order of the steps; these words may be used to guide the reader through the description of the methods. Further, any reference to claim elements in the singular, for example, using the articles "a," "an" or "the" is not to be construed as limiting the element to the singular.

Control elements may be implemented using computing devices (such as computer 46) comprising processors, memory and other components that have been programmed with instructions to perform specific functions or may be implemented in processors designed to perform the specified functions. A processor may be any programmable microprocessor, microcomputer or multiple processor chip or chips that can be configured by software instructions (applications) to perform a variety of functions, including the functions of the various embodiments described herein. In some computing devices, multiple processors may be provided. Typically, software applications may be stored in the internal memory before they are accessed and loaded into the processor. In some computing devices, the processor may include internal memory sufficient to store the application software instructions.

The various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

The hardware used to implement the various illustrative logics, logical blocks, modules, and circuits described in connection with the aspects disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but, in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration. Alternatively, some blocks or methods may be performed by circuitry that is specific to a given function.

The preceding description of the disclosed aspects is provided to enable any person skilled in the art to make or use the present invention. Various modifications to these aspects will be readily apparent to those skilled in the art, and the generic principles defined herein may be applied to other aspects without departing from the scope of the invention. Thus, the present invention is not intended to be limited to the aspects shown herein but is to be accorded the widest scope consistent with the principles and novel features disclosed herein.

What is claimed is:

1. A method of imaging an object, comprising:
positioning an object with an imaging bore of an O-shaped imaging gantry having at least one x-ray radiation source and at least two x-ray radiation detectors secured to a rotor that is rotatable within the gantry; and
obtaining simultaneous images of the object in multiple imaging planes, wherein obtaining the simultaneous images comprises:
directing x-ray radiation beams from the at least one x-ray radiation source through a common isocenter within the bore; and
detecting the x-ray radiation beams attenuated by an object within the bore at the at least two x-ray radiation detectors such that during a first time period, a first x-ray radiation detector is exposed to attenuated x-ray radiation from the object while a second x-ray radiation detector is not exposed to x-ray radiation and reads out imaging data collected during a previous exposure to attenuated x-ray radiation from the object, and during a second time period, the first x-ray radiation detector is not exposed to x-ray radiation and reads out imaging data collected during the first time period while the second x-ray radiation detector is exposed to attenuated x-ray radiation from the object, and the first time period and the second time period are each 0.1-100 milliseconds in duration.

2. The method of claim 1, wherein the object comprises a human or animal patient.

3. The method of claim 1, further comprising:
displaying bi-planar imaging data from the at least two detectors in real time.

4. The method of claim 1, further comprising:
reconstructing image data collected by at least one detector to provide a 3D tomographic image.

5. The method of claim 1, wherein directing x-ray radiation comprises directing x-ray radiation from at least two x-ray radiation sources, wherein each source is positioned opposite an x-ray radiation detector on the gantry.

6. The method of claim 1, further comprising:
providing high-voltage power to the at least one source using a high-voltage generator within the gantry.

7. The method of claim 6, wherein providing high-voltage power comprises providing pulses of high-voltage power to a plurality of x-ray radiation sources in succession.

8. The method of claim 6, wherein providing high-voltage power comprises providing pulses of high-voltage power to at least one x-ray radiation source during fluoroscopy and continuous high-voltage power to at least one x-ray radiation source during CT scanning.

9. The method of claim 1, further comprising:
rotating the at least one source and the at least two detectors around the gantry while obtaining images of the object.

10. The method of claim 9, wherein the at least one source and the at least two detectors are rotated around the gantry while at least one detector obtains images to provide a 3D CT scan.

11. The method of claim 10, wherein the 3D CT scan comprises single plane and/or bi-plane "cone beam" circular or helical scanning using one or more flat panel detectors.

12. The method of claim 10, further comprising:
translating the gantry relative to the object being imaged to provide a helical CT scan.

13. The method of claim 1, further comprising:
transmitting imaging data wirelessly from the gantry to an entity off the gantry.

14. The method of claim 1, wherein the object is a patient and the method further comprises:
translating the gantry relative to the patient to provide an arterial roadmap image of the patient.

15. The method of claim 14, wherein the arterial roadmap image is either single plane or bi-plane fluoroscopy roadmap image of a patient.

16. The method of claim 14, further comprising:
determining a velocity of translation of the gantry along a patient axis based on an image analysis of flow of contrast agent in an artery of the patient; and
translating the gantry at the determined velocity.

17. The method of claim 1, wherein the first period and the second period together form a cycle, and the cycle is continuously repeated during the imaging.

18. The method of claim 1, wherein the at least one x-ray radiation source comprises an x-ray tube and the at least two x-ray radiation detectors comprise at least one of a flat panel detector and a diagnostic-quality x-ray CT detector.

19. The method of claim 18, wherein the at least two detectors comprise flat panel detectors that are spaced 90° apart on the rotor.

20. The method of claim 1, wherein the imaging gantry is secured to a mobile base, the method further comprising:
translating the gantry with respect to the base in an imaging mode; and
translating the base and gantry together in a transport mode.

21. The method of claim 1, wherein the first time period and the second time period are each 5-30 milliseconds in duration.

* * * * *